United States Patent
Soni et al.

(10) Patent No.: US 11,049,239 B2
(45) Date of Patent: Jun. 29, 2021

(54) DEEP NEURAL NETWORK BASED IDENTIFICATION OF REALISTIC SYNTHETIC IMAGES GENERATED USING A GENERATIVE ADVERSARIAL NETWORK

(71) Applicant: GE Precision Healthcare LLC, Wauwatosa, WI (US)

(72) Inventors: Ravi Soni, San Ramon, CA (US); Min Zhang, San Ramon, CA (US); Zili Ma, San Ramon, CA (US); Gopal B. Avinash, San Ramon, CA (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 128 days.

(21) Appl. No.: 16/370,082

(22) Filed: Mar. 29, 2019

(65) Prior Publication Data

US 2020/0311913 A1    Oct. 1, 2020

(51) Int. Cl.
    *G06T 7/00*   (2017.01)
    *G06N 3/08*   (2006.01)
    *G16H 30/40*  (2018.01)

(52) U.S. Cl.
    CPC .......... *G06T 7/0012* (2013.01); *G06N 3/08* (2013.01); *G16H 30/40* (2018.01); *G06T 2207/20081* (2013.01); *G06T 2207/20084* (2013.01); *G06T 2207/20092* (2013.01)

(58) Field of Classification Search
    CPC ........ G06T 7/0012; G06T 2207/20092; G06T 2207/20081; G06T 2207/20084; G06N 3/08; G16H 30/40
    See application file for complete search history.

(56) References Cited

U.S. PATENT DOCUMENTS

| | | | |
|---|---|---|---|
| 10,504,504 B1* | 12/2019 | Meltzner | G10L 25/18 |
| 2015/0112182 A1* | 4/2015 | Sharma | A61B 5/7282 600/408 |
| 2015/0125049 A1* | 5/2015 | Taigman | G06T 15/205 382/118 |
| 2016/0307061 A1* | 10/2016 | Bulan | G06K 9/6256 |
| 2016/0379091 A1* | 12/2016 | Lin | G06K 9/00724 382/156 |
| 2017/0061625 A1* | 3/2017 | Estrada | G06N 3/0454 |
| 2018/0260957 A1* | 9/2018 | Yang | G06T 7/0012 |
| 2018/0322366 A1* | 11/2018 | Lim | G06K 9/6255 |

(Continued)

*Primary Examiner* — Ming Y Hon
(74) *Attorney, Agent, or Firm* — Amin, Turocy & Watson, LLP

(57) ABSTRACT

Techniques are provided for deep neural network (DNN) identification of realistic synthetic images generated using a generative adversarial network (GAN). According to an embodiment, a system is described that can comprise a memory that stores computer executable components and a processor that executes the computer executable components stored in the memory. The computer executable components can comprise, a first extraction component that extracts a subset of synthetic images classified as non-real like as opposed to real-like, wherein the subset of synthetic images were generated using a GAN model. The computer executable components can further comprise a training component that employs the subset of synthetic images and real images to train a DNN network model to classify synthetic images generated using the GAN model as either real-like or non-real like.

20 Claims, 11 Drawing Sheets

(56) References Cited

U.S. PATENT DOCUMENTS

| | | | |
|---|---|---|---|
| 2019/0080205 A1* | 3/2019 | Kaufhold | G06K 9/6257 |
| 2019/0147582 A1* | 5/2019 | Lee | G06T 11/00 |
| | | | 382/156 |
| 2019/0197358 A1* | 6/2019 | Madani | G06N 3/0481 |
| 2019/0259170 A1* | 8/2019 | Qi | G06T 7/73 |
| 2019/0272634 A1* | 9/2019 | Li | A61B 90/37 |
| 2019/0362835 A1* | 11/2019 | Sreenivasan | G06N 20/00 |
| 2020/0094074 A1* | 3/2020 | Chen | A61N 5/1037 |

* cited by examiner

DEEP NEURAL NETWORK BASED IDENTIFICATION OF REALISTIC SYNTHETIC IMAGES GENERATED USING A GENERATIVE ADVERSARIAL NETWORK

TECHNICAL FIELD

This application generally relates to artificial intelligence image analytics and more particularly to computer-implemented techniques for employing a deep neural network (DNN) for identification of realistic synthetic images generated using a generative adversarial network (GAN).

SUMMARY

The following presents a summary to provide a basic understanding of one or more embodiments of the invention. This summary is not intended to identify key or critical elements or to delineate any scope of the particular embodiments or any scope of the claims. Its sole purpose is to present concepts in a simplified form as a prelude to the more detailed description that is presented later. In one or more embodiments described herein, systems, computer-implemented methods, apparatus and/or computer program products are provided that employ a DNN for identification of realistic synthetic images generated using a GAN.

According to an embodiment, a system can comprise a memory that stores computer executable components and a processor that executes the computer executable components stored in the memory. The computer executable components can comprise, a first extraction component that extracts a subset of synthetic images classified as non-real like as opposed to real-like, wherein the subset of synthetic images were generated using a GAN model. The computer executable components can further comprise a training component that employs the subset of synthetic images and real images to train a DNN network model to classify synthetic images generated using the GAN model as either real-like or non-real like. In one or more embodiments, the DNN comprise a very deep convolutional neural network.

In various implementations, the computer executable components further comprise a synthetic image generator that generates first synthetic images using the GAN model, and an annotation component that labels the first synthetic images as either real-like or non-real like. With these implementations, wherein the first extraction component extracts the subset of synthetic images from the first synthetic images in response to labeling of respective synthetic images included in the subset set as non-real like. In some embodiments, the annotation component labels the first synthetic images based on reception of manual input that classifies the first synthetic images as either real-like or non-real-like.

In one or more embodiments, the synthetic image generator further generates second synthetic images using the GAN model, and the computer executable components further comprise an inference component that employs the DNN model to classify the second synthetic images as either real-like or non-real-like. With these embodiments, the subset of synthetic images comprises a first subset of synthetic images, and the computer executable components further comprise a second extraction component that extracts, from the second synthetic images, a second subset of synthetic images classified as real-like as opposed to non-real-like by the inference component. In some implementations, the computer executable components further comprise a target model training component that employs the second subset of synthetic images to train a machine learning model to perform artificial intelligence analytics on real images. For example, in various embodiments, the first synthetic images, the second synthetic images and the real images comprise medical images, and the target model training component employs the second subset of synthetic images to train the machine learning model to diagnose medical conditions reflected in the real images.

In some embodiments, elements described in connection with the system can be embodied in different forms such as a computer-implemented method, a computer program product, or another form.

DETAILED DESCRIPTION

Figure 1:
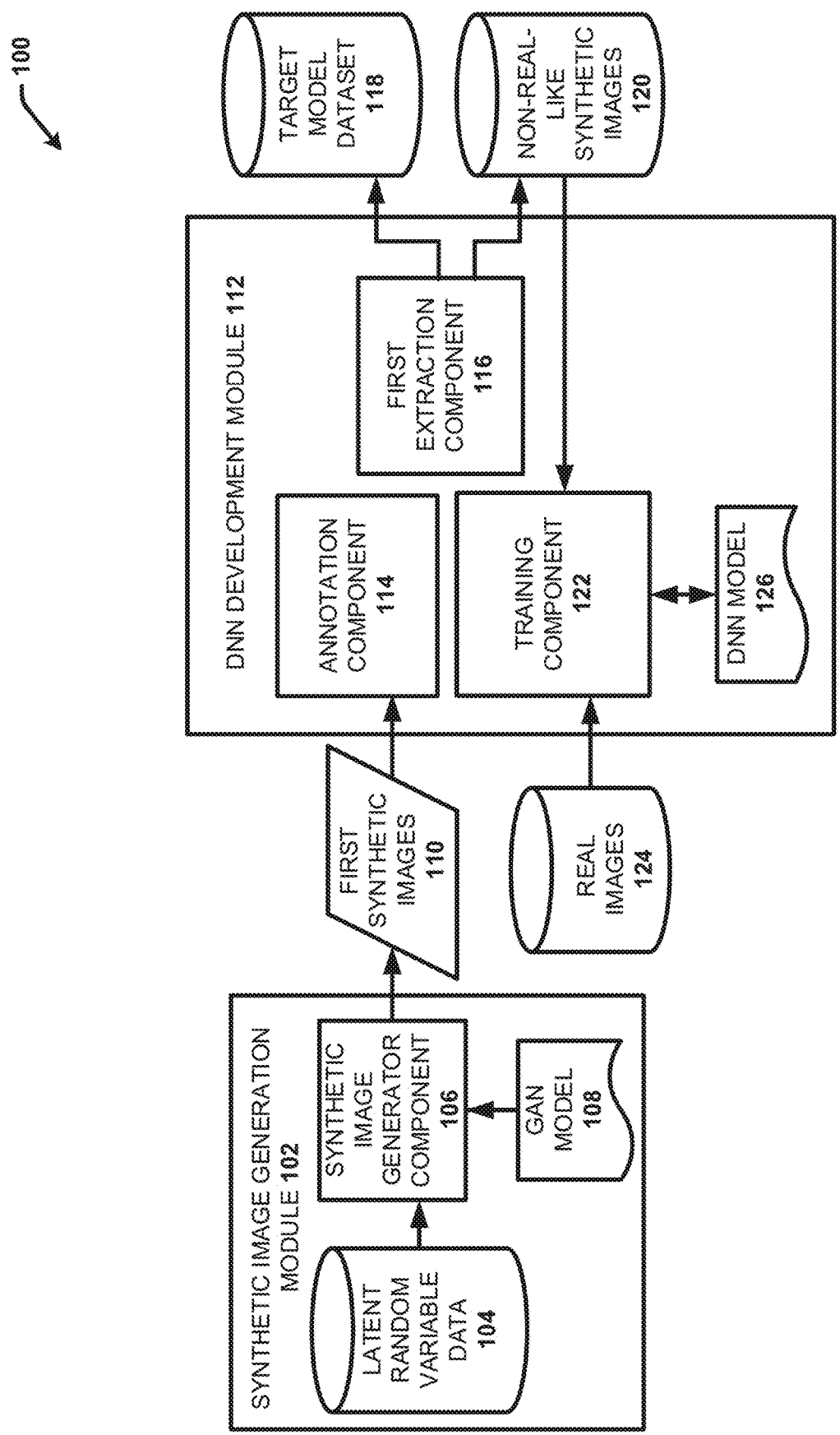
FIG. 1 illustrates a block diagram of an example, non-limiting system that facilitates developing a deep neural network (DNN) model that facilitates identifying realistic synthetic images generated using a GAN in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

The subject disclosure provides systems, computer-implemented methods, apparatus and/or computer program products that facilitate automatically identifying and extracting realistic synthetic images as opposed to non-realistic synthetic images using a deep neural network (DNN) model trained on real images and previously identified synthetic images classified as non-real-like. The synthetic images can include images generated using a generative adversarial network (GAN) model. The identified and extracted realistic synthetic images can be combined with real images to form a comprehensive training dataset that can be used to train a target machine learning model to perform various automated image analysis functions. For example, in various embodiments, synthetic images can include synthetic medical images generated using a GAN model and the target machine learning model can include a medical image analysis model configured to automatically evaluate and diagnose medical conditions reflected in real (e.g., not synthetic) medical images.

In this regard, artificial intelligence (AI) and machine learning (ML) is a rapidly progressing technical field impacting a wide range of industries. Advancements in machine learning technologies, such as deep neural networks (DNN)s, have recently shown impressive performance, sometimes exceeding humans, in various AI domains, including computer vision, speech, natural language processing (NPL), bioinformatics, drug design, medical image analysis, and more. These achievements were made possible by significant improvement in computation power as well as the availability of massive scale annotated datasets, leading to better inferencing performance than traditional models. However, one of the fundamental problems in data-driven based machine learning approaches such as DNNs is that the final model inferencing capability is limited by the scope of the training data used to develop the model. With respect to the medical imaging sector, due to various regulatory and privacy restrictions associated with accessing and using patient data, it can be difficult to obtain enough medical images for model training that provide a comprehensive representation of a target medical condition across different patient populations. As a result, techniques for generating synthetic medical images have been developed to increase the amount and distribution of the available training images.

One technique for generating synthetic medical images involves the usage of generative adversarial network (GAN) models. GAN models are powerful latent variable models that can be used to learn complex real-world data distributions. In computer vision, GANs have emerged as one of the dominant approaches for generating realistically looking samples after learning the training image data distribution. However, it is very challenging to generate high quality synthetic images. For example, in healthcare, every patient and their medical conditions are different from the rest of the population. Many variables play a vital role in the image appearance, such as medical history, family history, daily activity, or work environment. During the GAN model training, the sole responsibility of the algorithm is to mimic input data distribution so that the output data distribution is similar to the input data distribution.

Different types of GAN models have been explored to increase the realistic quality and resolution of the output synthetic images. However, GANs can be hard to train in practice, and despite improvements, it has been observed that the optimization does not lead to convergence all the time. One common failure mode involves the generator collapsing to produce only a single sample or a small family of very similar samples. Although some GAN models have demonstrated local convergence on training for absolutely continuous data and generator distributions, even if the convergence is achieved there is a possibility that the generator will produce non-realistic synthetic images. These non-realistic synthetic images can contaminate the training dataset and significantly reduce the performance of the final machine learning model trained thereon.

The disclosed subject matter provides techniques for automatically identifying and removing these non-realistic looking GAN model generated synthetic images from a training dataset, particularly under the context in which the GAN model has demonstrated convergence. In one or more embodiments, the disclosed techniques involve training a DNN to filter non-realistic looking synthetic images. In some implementations, the DNN model can include a very complex convolutional DNN model that is a binary classifier. The trained model can provide for classifying synthetic images as either real-like (e.g., realistic looking) or non-real-like (e.g., not realistic looking). For example, as applied to medical images, the trained DNN model can mimic a radiologist which classifies realistically and non-realistically looking synthetic medical images. In some embodiments in which the DNN model is trained to classify synthetic medical images in this way, the DNN model is referred to herein as a virtual radiologist network (VRN).

This problem can be modelled as a fine-grained classification problem. In this regard, the DNN model can be trained using real (e.g., not synthetic) images and non-real-like synthetic images previously classified and labeled as being non-real-like. In some embodiments, the non-real-like synthetic training images can be automatically identified and selected from a set of GAN model generated synthetic images using AI techniques. For example, the non-real-like synthetic images can be identified and extracted from real-like synthetic images using one or more supervised, semi-supervised, or unsupervised learning machine learning models. In other embodiments, the non-real-like synthetic training images can be manually labeled. For example, in implementations in which the synthetic images comprise medical images, a radiologist expert and//or a non-domain expert can manually review the synthetic images as label them either real-like or non-real-like.

Once there are enough synthetic training images for non-real-like class, the DNN model can be trained, using real images in the training set for the real-like image class. The trained DNN model can then be used to separate real-like and non-real-like synthetic images by running in an inferencing mode. All the categorized real-like synthetic images can then be used to augment training datasets for clinical models to improve their performance.

Various embodiments of the disclosed subject matter are directed to filtering real-like verses non-real-like synthetic medical images. These can include various types of synthetic medical images associated with a variety of different capture modalities, including, (but not limited to), x-ray, computerized tomography (CT), mammography (MG), magnetic resonance imaging (MRI), and the like. However, the disclosed techniques are not limited to medical images. In this regard, the disclosed techniques can be applied to automatically classify essentially any type of GAN model based synthetic image as real-like or non-real-like.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting system 100 that facilitates developing a DNN model that for identifying realistic synthetic images generated using a GAN in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

For example, system 100 includes a synthetic image generation module 102 and a DNN development module 112. The synthetic image generation module 102 and the DNN development module 112 can respectively be and include machine-executable components stored in memory (not shown) associated with the one or more machines (not shown). The memory can further be operatively coupled to at least one processor (not shown), such that the components (e.g., the synthetic image generation module 102, the DNN development module 112, and the components associated therewith), can be executed by the at least one processor to perform the operations described. Examples of said and memory and processor as well as other suitable computer or computing-based elements, can be found with reference to FIG. 11, and can be used in connection with implementing one or more of the systems or components shown and described in connection with FIG. 1 or other figures disclosed herein.

System 100 and/or one or more components of the system 100 or other systems disclosed herein can be employed to use hardware and/or software to solve problems that are highly technical in nature, that are not abstract, and that cannot be performed as a set of mental acts by a human. In this regard, system 100 and/or components of system 100 can employ a GAN model (e.g., GAN model 108) to generate synthetic images and further train a DNN model (e.g., DNN model 126) to automatically identify and extract realistic synthetic images as opposed to non-realistic looking synthetic images. These DNN model selected real-like synthetic images can be used for further clinical model training. Prior solution involved asking domain experts (e.g., radiologists in the context of medical images) or non-domain experts to manually review and segregate the real-like and not real-like synthetic images based on visual observations. They then chose the real-like images for clinical model training. However, this is highly labor intensive and thus not a scalable solution as there is a need of reviewing the synthetic images again when they are generated for different clinical model trainings. Technically, a trained GAN model can generate countably infinite synthetic images that can be used to augment training datasets for clinical AI model training. Therefore, the trained DNN model can be used to filter these countably infinite synthetic images appropriately and select only the real-like images to use for model training.

Accordingly, system 100 and/or components of system 100 (and other systems described herein) can facilitate improving the quality and quantity of training data sets by augmenting them with realistic looking synthetic images in an efficient an automated manner. As a result, system 100 and/or components of system 100 provide for improving the performance accuracy and specificity of final target models trained using the real-like synthetic images. In this regard, system 100 and/or components of system 100 or other systems described herein can be employed to solve new problems that arise through advancements in technology, computer networks, the Internet, and the like, particularly advancement in AI solutions in which real-like synthetic images can be used to augment model training and performance.

In this regard, the synthetic image generation module 102 can provide for generating synthetic images. The synthetic image generation module 102 can include a synthetic image generator component 106, a database or datastore comprising latent random variable data 104, and a GAN model 108. The synthetic image generator component 106 can be configured to apply the GAN model 108 to the latent random variable data 104 to generate the synthetic images. For example, in the embodiment shown, the synthetic image generator component 106 can generate first synthetic images 110 using the GAN model 108 and the latent random variable data 104. In various exemplary embodiments, the first synthetic images 110 can include synthetic medical images.

GAN models such as GAN model 108 can be configured to generate realistically looking synthetic images after learning the training image data distribution. A GAN generally involves two neural networks, a generative network and a discriminative network. The generator produces a sample, such as a synthetic image, from latent code (e.g., latent random variable data 104). The distribution of the synthetic images generated from the latent code should ideally be indistinguishable from the training distribution. Since it is generally infeasible to engineer a function that tells where that is the case, a discriminator network is trained to do the assessment. Because neural networks are differentiable, a gradient can be used to steer both networks to the right direction. The generator network is of main interest. The discriminator network is an adaptive loss function that is relatively week classifier. The discriminator network gets discarded once the generator network has been trained. In this regard, the GAN model 108 can included the trained generator network of the model configured to generate the synthetic images.

During the GAN model training, the sole responsibility of the algorithm is to mimic input data distribution so that the output data distribution is similar to the input data distribution. However, GANs can be hard to train in practice, and despite improvements, it has been observed that the optimization does not lead to convergence all the time. One common failure mode involves the generator collapsing to produce only a single sample or a small family of very similar samples. Although some GAN models have demonstrated local convergence on training for absolutely continuous data and generator distributions, even if the convergence is achieved there is a possibility that the generator will produce non-realistic synthetic images.

Figure 2:
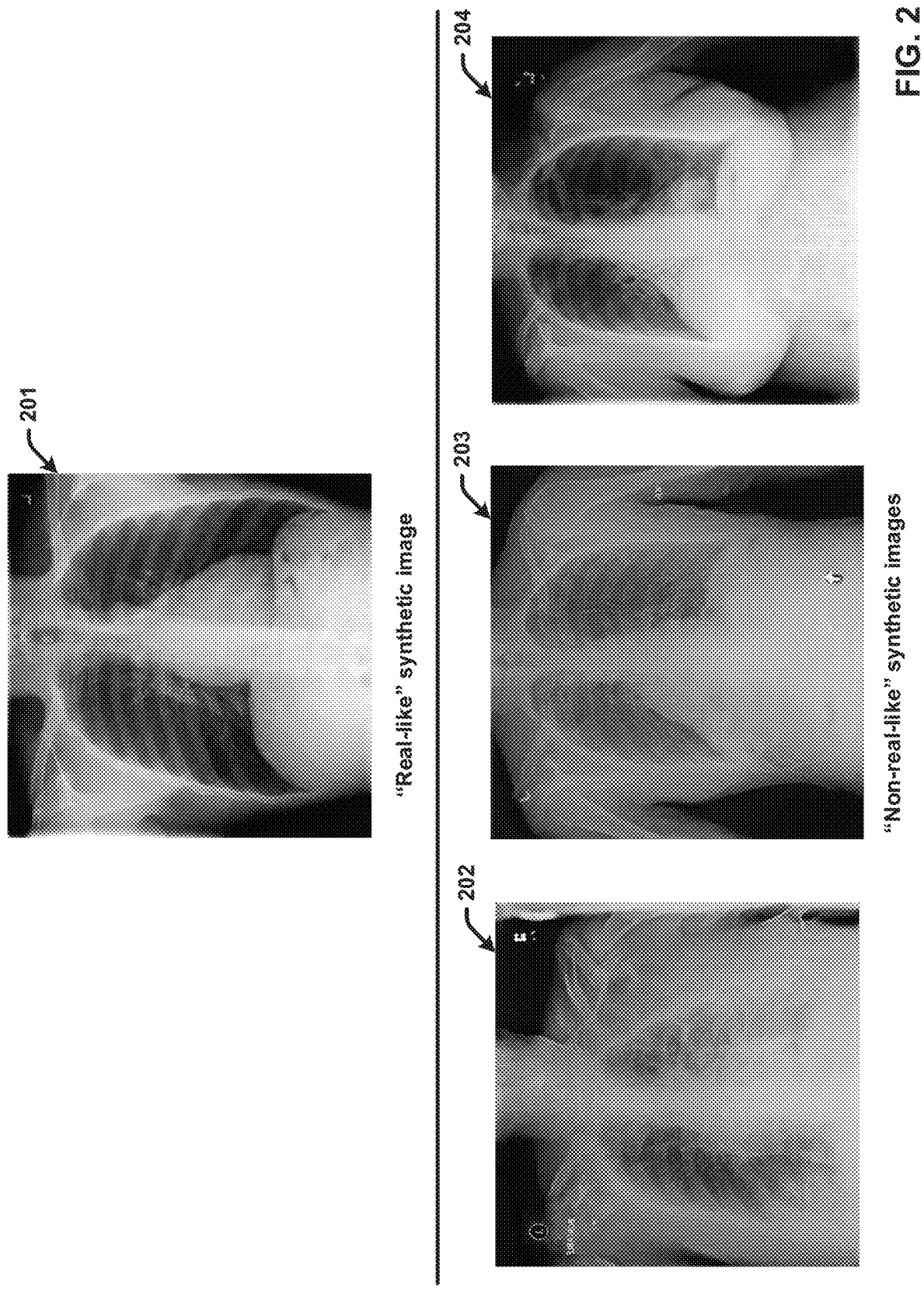
FIG. 2 illustrates example real-like and non-real-like synthetic medical images generated using a GAN model in accordance with one or more embodiments of the disclosed subject matter.

For example, FIG. 2 illustrates example real-like and non-real-like synthetic medical images generated using a GAN model (e.g., GAN model 108) in accordance with one or more embodiments of the disclosed subject matter. The synthetic images shown in FIG. 2 were generated by a GAN model that had converged. The synthetic images respectively correspond to real chest x-rays. Image 201 provides an example real-like looking synthetic image generated by the GAN model and images 202-204 demonstrate non-real-like synthetic images generated by the same GAN model. As it can be noticed by comparison with image 201, image 202 has a lot of irregularities such as mangled lung, ribs, and heart features. Images 203 and 204 may seem very real-like at first glance, but they also possess unavoidable issues such as vanished rib parts, two hearts like features, etc.

With reference again to FIG. 1, the DNN development module 112 can receive and process the first synthetic images 110 to identify and segregate the non-real-like synthetic images from the real-like synthetic images. The DNN development module 112 can further employ the non-real-like synthetic images 120 to train a DNN model 126 to automatically classify synthetic images as either real-like or non-real-like. In the embodiment shown the DNN development module 112 can include annotation component 114, first extraction component 116 and training component 122.

The annotation component 114 can facilitate annotating or labeling the first synthetic images 110 as either real-like or non-real-like. In some embodiments, the annotation component 114 can label the first synthetic images as either real-like or non-real-like based on reception of user input identifying or classifying the respective images as either real-like or non-real-like. For example, in some embodiments, the first synthetic images 110 can be manually reviewed and annotated by a domain expert (e.g., a radiologist) or non-domain expert. With these embodiments, the annotation component 114 can apply or otherwise associate labels (e.g., metadata) with the respective first synthetic images that classifies them as either real-like or non-real-like based on the manual input.

In other embodiments, the annotation component 114 can employ AI and one or more machine learning techniques to label the respective first synthetic images 110 as either real-like or non-real-like. With these embodiments, the annotation component 114 can include provide for automatically (e.g., without manual input) classifying the first synthetic images 110 as either real-like or non-real-like using one or more machine learning models. For example, the one or more machine learning class models can include one or more AI/machine learning classification models configured to identify distinguishing features associated with the synthetic images that can be used to classify them as real-like or non-real-like. With these embodiments, the annotation component 114 can employ the one or more machine learning classification models to classify respective images of the first synthetic images as either real-like or non-real-like, and then label the respective images according to the classification determined by using the one or more machine learning models classification models.

In this regard, the one or more machine learning classification models can employ various classification (explicitly and/or implicitly trained) schemes and/or systems (e.g., support vector machines, neural networks, expert systems, Bayesian belief networks, fuzzy logic, data fusion engines, etc.) in connection with classifying a synthetic image as either real-like or non-real-like. For example, the one or more machine learning classification models can map an input attribute vector, x=(x1, x2, x4, x4, xn), to a confidence that the input belongs to a class of either real-like or non-real-like, such as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches that can be used by the annotation component 114 to classify and label the first synthetic images 110 as real-like or non-real-like can include but are not limited to, naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

Regardless of the manner in which the first synthetic images 110 are classified and labeled as either real-like or non-real-like (e.g., using manual annotation input and/or automatically using one or more AI based classification techniques), the first extraction component 116 can further filter the synthetic images to separate the real-like synthetic images and the non-real-like synthetic images. In various embodiments, the first extraction component can identify and extract all (or in some implementations one or more) of the first synthetic images 110 classified/labeled as non-real-like and collect them into a training dataset. In the embodiment shown, the extracted non-real-like synthetic images are shown in a separate database comprising (only) non-real-like synthetic images 120. The first extraction component 116 can also identify and extract all (or in some implementations one or more) of the first synthetic images classified/labeled as real-like add them to the target model dataset 118. For example, the target model dataset can include all of the "good" images that will be used to train a target model, such as a clinical model designed to diagnose medical condition reflected in real (not synthetic) images.

The training component 122 can further employ the non-real-like synthetic images 120 and real images 124 to train a DNN model 126 to classify synthetic images as either real-like or non-real-like. Unlike the discriminator network used to train the GAN model 108 (which is a week classifier), the DNN model 126 can include a very deep convolutional neural network that is a binary classifier. In this regard, the training component 122 can train the DNN model 126 to distinguish between non-real-like synthetic images using the non-real-like synthetic images 120 to represent the "non-real" class and real images (e.g., not synthetic) to represent the real class. For example, in implementations in which the non-real-like synthetic images are medical images of a specific type (e.g., chest x-rays), the real images 124 can include real medical images of the same specific type. As described in greater detail infra, once the DNN model 126 training is complete, the DNN model 126 can be used to automatically classify synthetic images generated using the GAN model 108 as either real-like or non-real-like.

Figure 3:
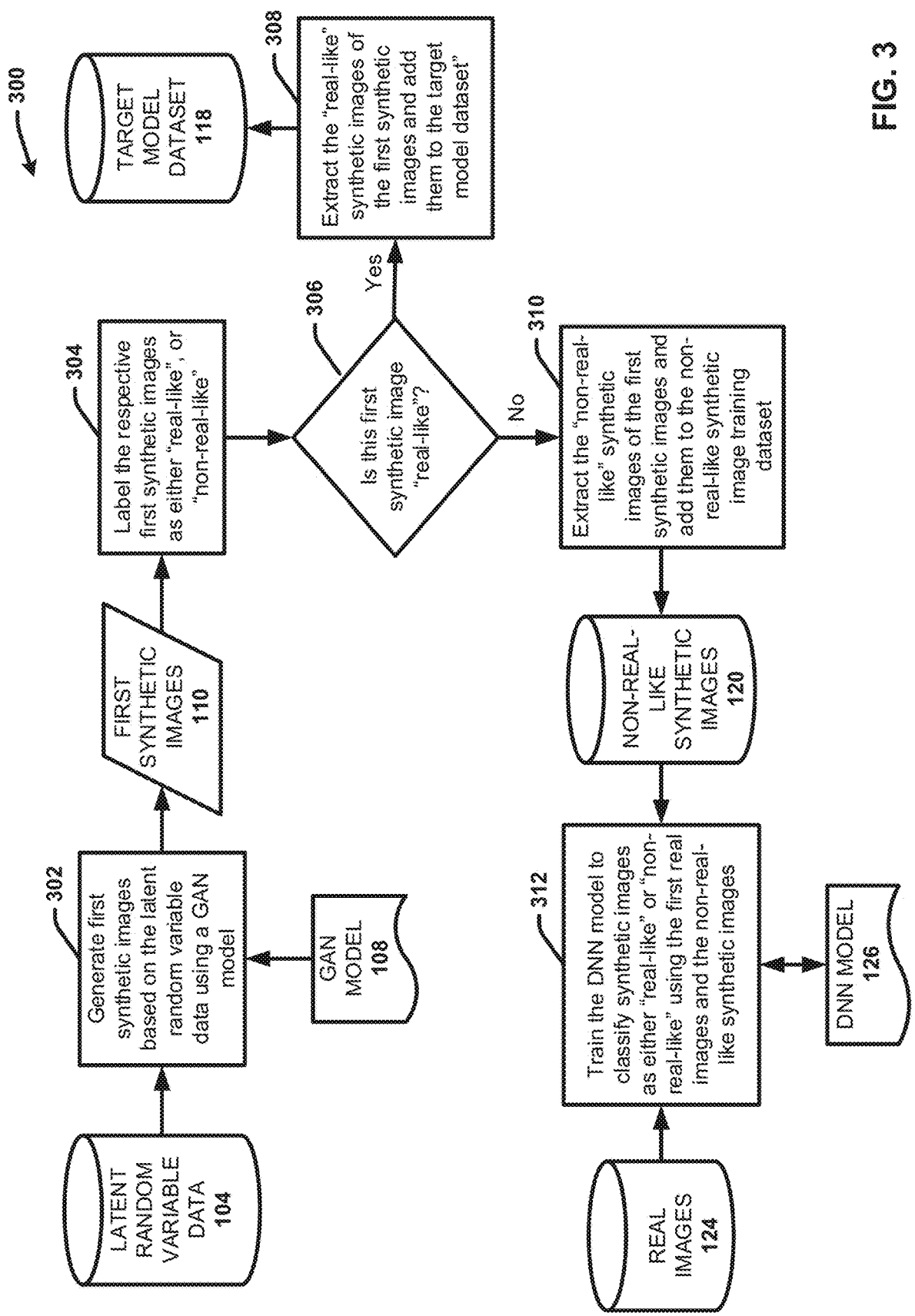
FIG. 3 illustrates a flow diagram of an example, non-limiting process for developing a DNN model that facilitates identifying realistic synthetic images generated using a GAN in accordance with one or more embodiments of the disclosed subject matter.

FIG. 3 illustrates a flow diagram of an example, non-limiting process 300 for developing a DNN model (e.g., DNN model 126) that facilitates identifying realistic synthetic images generated using a GAN in accordance with one or more embodiments of the disclosed subject matter. In one or more embodiments, process 300 provide an exemplary process that can be performed by system 100 to generate DNN model 126. Repetitive description of like elements employed in respective embodiments is omitted for sake of brevity.

At 302, first synthetic images 110 can be generated (e.g., via synthetic image generator component 106) based on the latent random variable data 104 using a GAN model 108. At 304, the respective first synthetic images of the first synthetic images 110 can be labeled as either real-like or non-real-like (e.g., via annotation component 114). For example, in some embodiments, the respective first synthetic images can be manually reviewed and annotated (e.g., by a radiologist or non-domain expert). In other embodiments, one or more machine learning techniques can be applied to automatically classify the synthetic images as either real-like or non-real-like. At 306, each (or in some implementations one or more) of the first synthetic images can be filtered based on their classification as either real-like or non-real like. For example, at 306, if a synthetic image is classified/labeled as real-like, then at 308, the real-like synthetic image can be extracted (e.g., via first extraction component 116) and added to the target model dataset 118.

However, if at 306, a first synthetic image is classified as non-real-like, the non-real-like synthetic image can be extracted and added to the non-real-like synthetic images 120 training dataset. Once there is enough non-real-like synthetic images 120 (e.g., based on a defined minimum amount, or another deterministic criterion), then at 312, the DNN model can be trained (e.g., via training component 122). In this regard, the DNN model 126 can be trained to classify synthetic images as either real-like or non-real-like using the real images 124 (e.g., not synthetic images) and the non-real-like synthetic images 120 as input.

Figure 4:
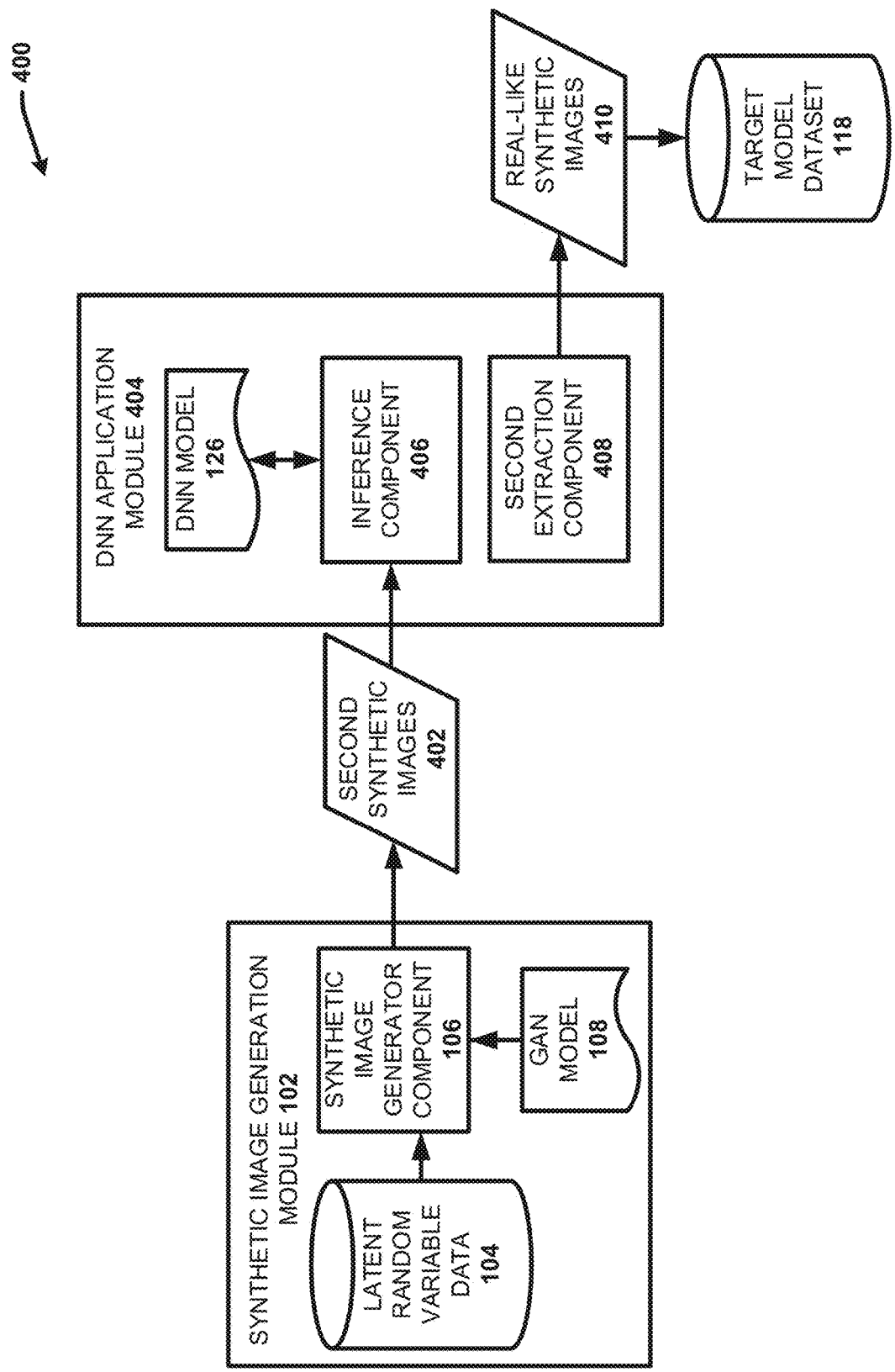
FIG. 4 illustrates a block diagram of an example, non-limiting system that facilitates employing a DNN model to identify realistic synthetic images generated using a GAN model in accordance with one or more embodiments of the disclosed subject matter.

FIG. 4 illustrates a block diagram of an example, non-limiting system 400 that facilitates employing a DNN model to identify realistic synthetic images generated using a GAN model in accordance with one or more embodiments of the disclosed subject matter. System 400 includes at least some same or similar components as system 100. In one or more embodiments, system 100 can include system 400, or vice versa. Repetitive description of like elements employed in respective embodiments is omitted for sake of brevity.

Similar to system 100, system 400 can include the synthetic image generation module 102 and the target model dataset 118. System 400 further include a DNN application module 404 which can include an inference component 406 and a second extraction component 408. The DNN application module 404 can be and include machine-executable components stored in memory (not shown) associated with the one or more machines (not shown). The memory can further be operatively coupled to at least one processor (not shown), such that the components (e.g., DNN application module 404 and the components associated therewith), can be executed by the at least one processor to perform the operations described. Examples of said and memory and processor as well as other suitable computer or computing-based elements, can be found with reference to FIG. 11, and can be used in connection with implementing one or more of the systems or components shown and described in connection with FIG. 4 or other figures disclosed herein.

The DNN application module 404 can be configured to apply the DNN model 126 after training and development thereof (e.g., by the DNN development module 112) to separate real-like and non-real-like synthetic images by running in an inferencing mode. In this regard, after the DNN model 126 has been trained, the synthetic image generation module 102 can generate second synthetic images using the synthetic image generator component 106, the GAN model 108 and the latent random variable data 104. The inference component 406 can further employ the DNN model 126 to classify each (or in some implementations one or more) of the second synthetic images as either real-like or non-real-like. The second extraction component 408 can further extract all (or in some implementations one or more) of the second synthetic images classified as real-like, depicted in FIG. 4 as real-like synthetic images 410. These real-like synthetic images can further be added to the target model dataset 118. In some embodiments, the second extraction component 408 can discard the second synthetic images 402 classified as non-real-like.

Figure 5:
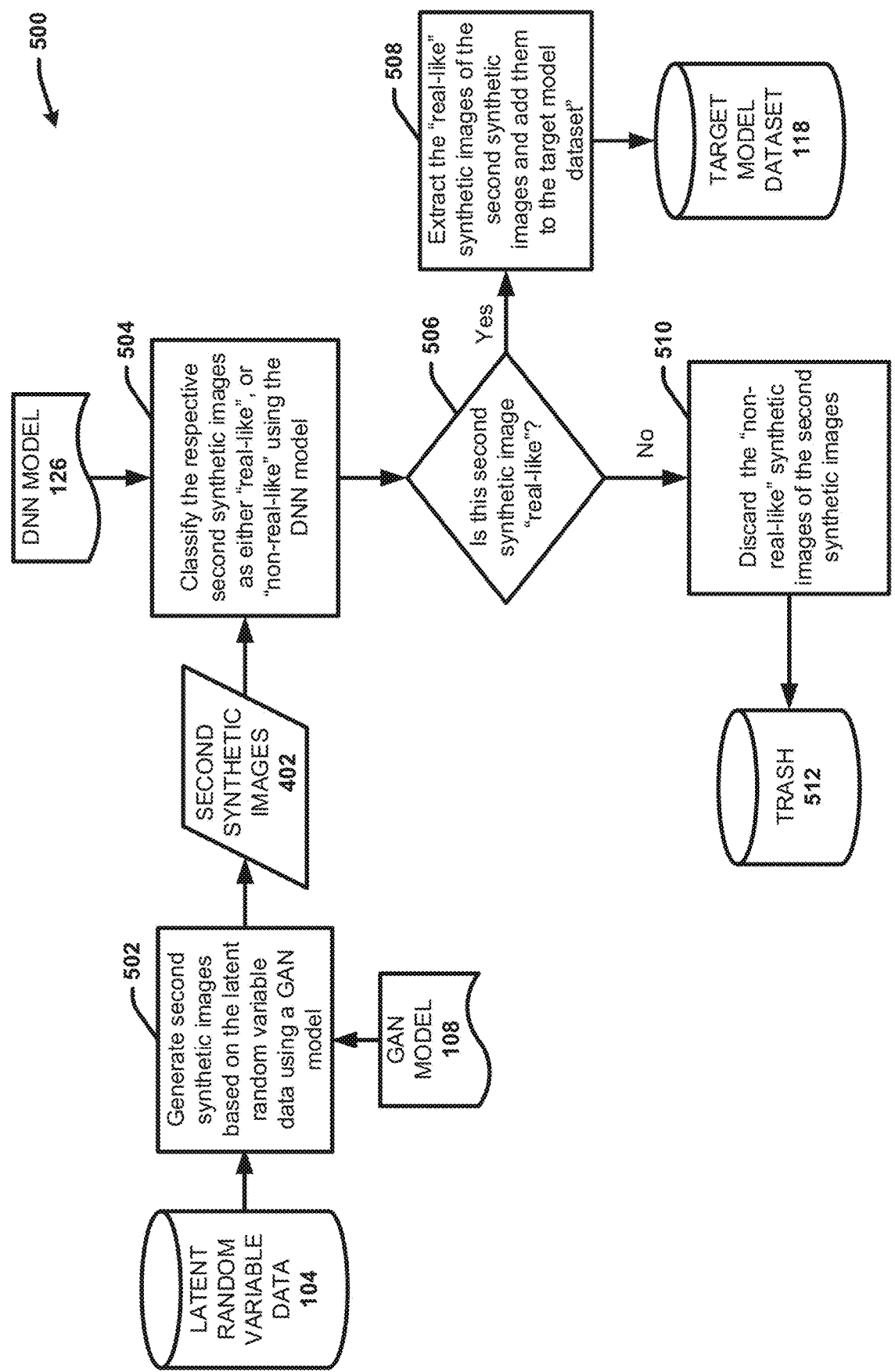
FIG. 5 illustrates a flow diagram of an example, non-limiting process for employing a DNN model to identify realistic synthetic images generated using a GAN model in accordance with one or more embodiments of the disclosed subject matter.

FIG. 5 illustrates a flow diagram of an example, non-limiting process for employing a DNN model to identify realistic synthetic images generated using a GAN model in accordance with one or more embodiments of the disclosed subject matter. In one or more embodiments, process 500 provide an exemplary process that can be performed by system 400 to generate a target model dataset that includes real-like synthetic images and excludes non-real-like synthetic images (e.g., target model dataset 118). Repetitive description of like elements employed in respective embodiments is omitted for sake of brevity.

At 502, second synthetic images 402 can be generated (e.g., via synthetic image generator component 106) based on the latent random variable data 104 using a GAN model 108. At 504, using the DNN model 126, the respective second synthetic images 402 can classified as either real-like or non-real-like (e.g., by the inference component 406). At 506, each (or in some implementations one or more) of the second synthetic images can be filtered based on their classification as either real-like or non-real like. For example, at 506, if a second synthetic image is classified as real-like, then at 508, the real-like synthetic image can be extracted (e.g., via second extraction component 408) and added to the target model dataset 118. However, if at 506, a second synthetic image is classified as non-real-like, the non-real-like synthetic image can be discarded (e.g., added to the trash 512).

Figure 6:
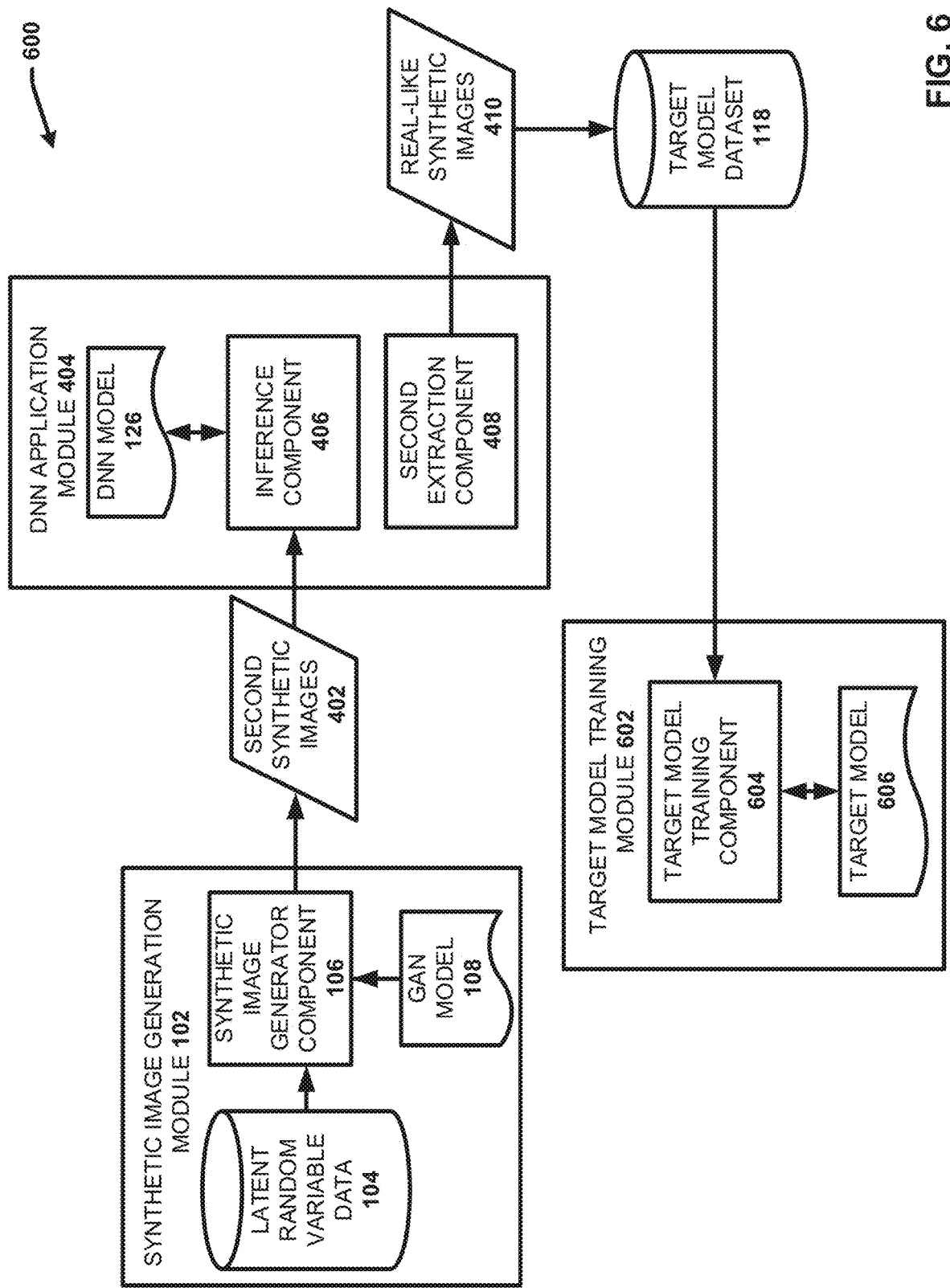
FIG. 6 illustrates a block diagram of an example, non-limiting system that facilitates training a machine learning model using realistic synthetic images to make inferences on real images in accordance with one or more embodiments of the disclosed subject matter.

FIG. 6 illustrates a block diagram of an example, non-limiting system 600 that facilitates training a machine learning model using realistic synthetic images to make inferences on real images in accordance with one or more embodiments of the disclosed subject matter. System 600 includes same or similar components as system 400 with the addition of target model training module 602 and second real images 608. In one or more embodiments, system 100 can include system 600, or vice versa. Repetitive description of like elements employed in respective embodiments is omitted for sake of brevity.

The target model training module 602 can be and include machine-executable components stored in memory (not shown) associated with the one or more machines (not shown). The memory can further be operatively coupled to at least one processor (not shown), such that the components (e.g., the target model training module 602 and the components associated therewith), can be executed by the at least one processor to perform the operations described. Examples of said and memory and processor as well as other suitable computer or computing-based elements, can be found with reference to FIG. 11, and can be used in connection with implementing one or more of the systems or components shown and described in connection with FIG. 6 or other figures disclosed herein.

The target model training module 602 can include target model training component 604 and a target model 606. The target model training component 604 be configured to apply the target model dataset 118, including the real-like synthetic images 410, to train the target model 606. For example, in one embodiment, the target model 606 can include a machine learning model configured to identify and/or diagnose medical conditions reflected in real medical images (e.g., in a clinical context). With these embodiments, the target model dataset 118 can include real-like synthetic medical images and the target model training component 604 can train the target model 606 to identify and/or diagnose the medical conditions in real medical images based on representations of the medical conditions reflected in the real-like synthetic images 410. In some implementations, the target model dataset 118 and also include real images. In this regard, the real-like synthetic images 410 can be used to increase the size and distribution of the training images in scenarios in which the real medical images for the training sample are unavailable or are limited. As a result, the final performance of the (trained) target model 606 can be improved.

Figure 7:
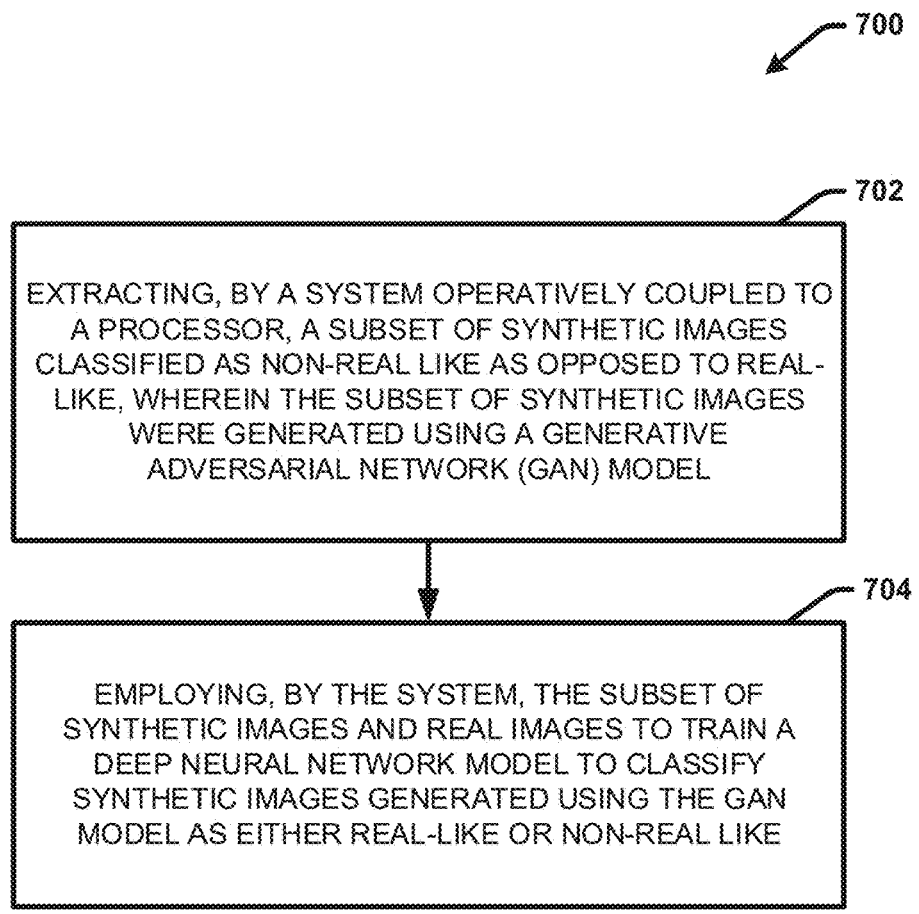
FIG. 7 provides a flow diagram of an example, non-limiting computer-implemented method that for developing a DNN model that facilitates identifying realistic synthetic images generated using a GAN in accordance with one or more embodiments of the disclosed subject matter.

FIG. 7 provides a flow diagram of an example, non-limiting computer-implemented method 800 that facilitates DNN identification of realistic synthetic images generated using a GAN in accordance with one or more embodiments of the disclosed subject matter. Repetitive description of like elements employed in respective embodiments is omitted for sake of brevity.

At 702, a system operatively coupled to a processor (e.g., system 100, or the like), can extract a subset of synthetic images (e.g., non-real-like synthetic images 120) classified as non-real like as opposed to real-like (e.g., using first extraction component 116), wherein the subset of synthetic images were generated (e.g., by the synthetic image generation module 102) using a GAN model (e.g., GAN model 108). At 702, the system can employ the subset of synthetic images and real images (e.g., real images 124) to train (e.g., using training component 122) a DNN model (e.g., DNN model 126) to classify synthetic images generated using the generative adversarial network model as either real-like or non-real like.

Figure 8:
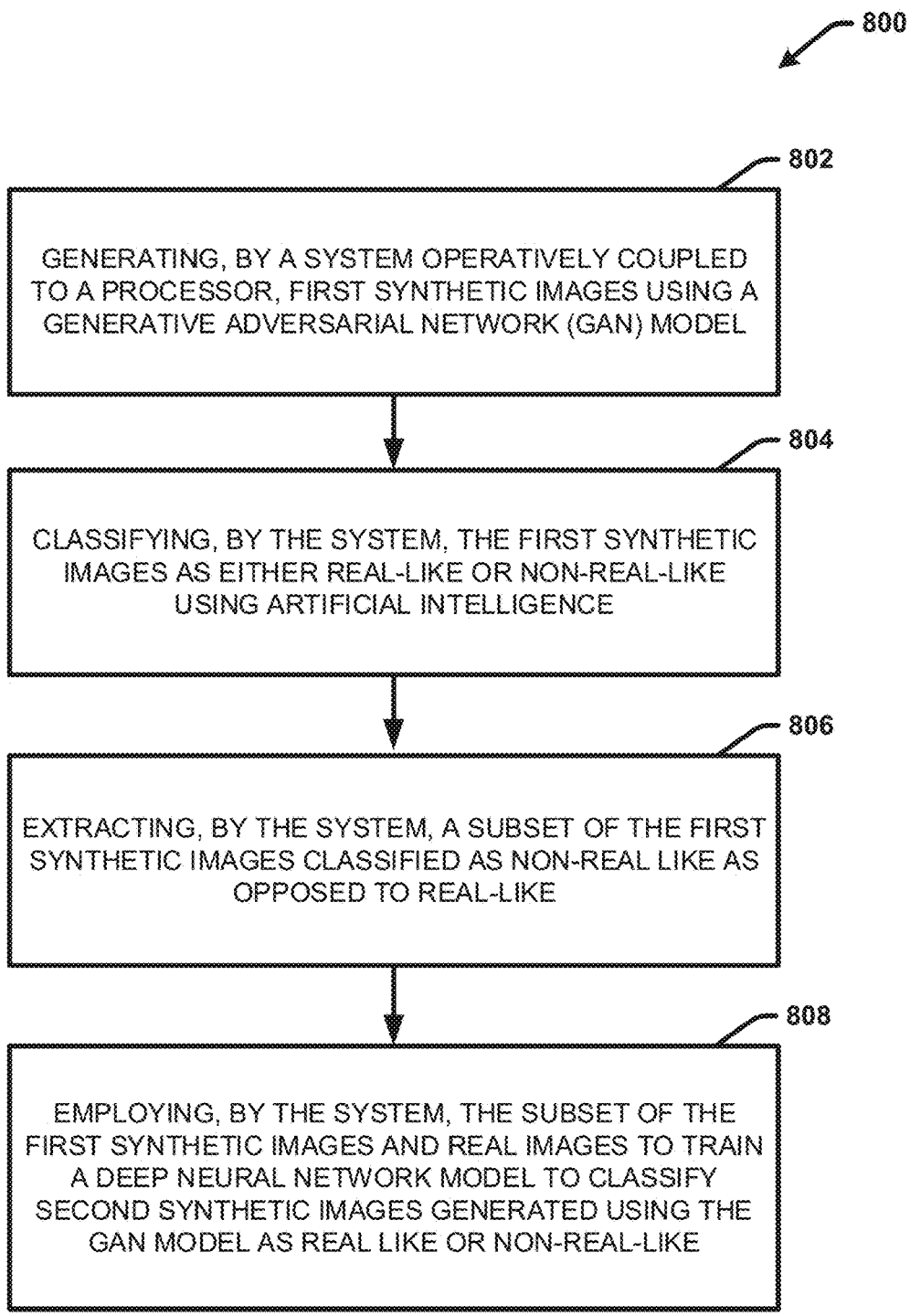
FIG. 8 provides a flow diagram of another example, non-limiting computer-implemented method that facilitates evaluating and defining the scope of data-driven deep learning models in accordance with one or more embodiments of the disclosed subject matter.

FIG. 8 provides a flow diagram of another example, non-limiting computer-implemented method 800 that facilitates DNN identification of realistic synthetic images generated using a GAN in accordance with one or more embodiments of the disclosed subject matter. Repetitive description of like elements employed in respective embodiments is omitted for sake of brevity.

At 802, a system operatively coupled to a processor (e.g., system 100, or the like), can generate (e.g., using the synthetic image generation module 102), first synthetic images (e.g., first synthetic images 110) using a GAN model (e.g., GAN model 108). At 804, the system can classify the first synthetic images as either real-like or non-real-like using artificial intelligence. At 806, the system can extract (e.g., using first extraction component 116) a subset of the first synthetic images (e.g., non-real-like synthetic images 120) classified as non-real like as opposed to real-like (e.g., using first extraction component 116). At 808, the system can employ the subset of the first synthetic images and real images (e.g., real images 124) to train (e.g., using training component 122) a DNN model (e.g., DNN model 126) to classify second synthetic images generated using the GAN model as either real-like or non-real like.

Figure 9:
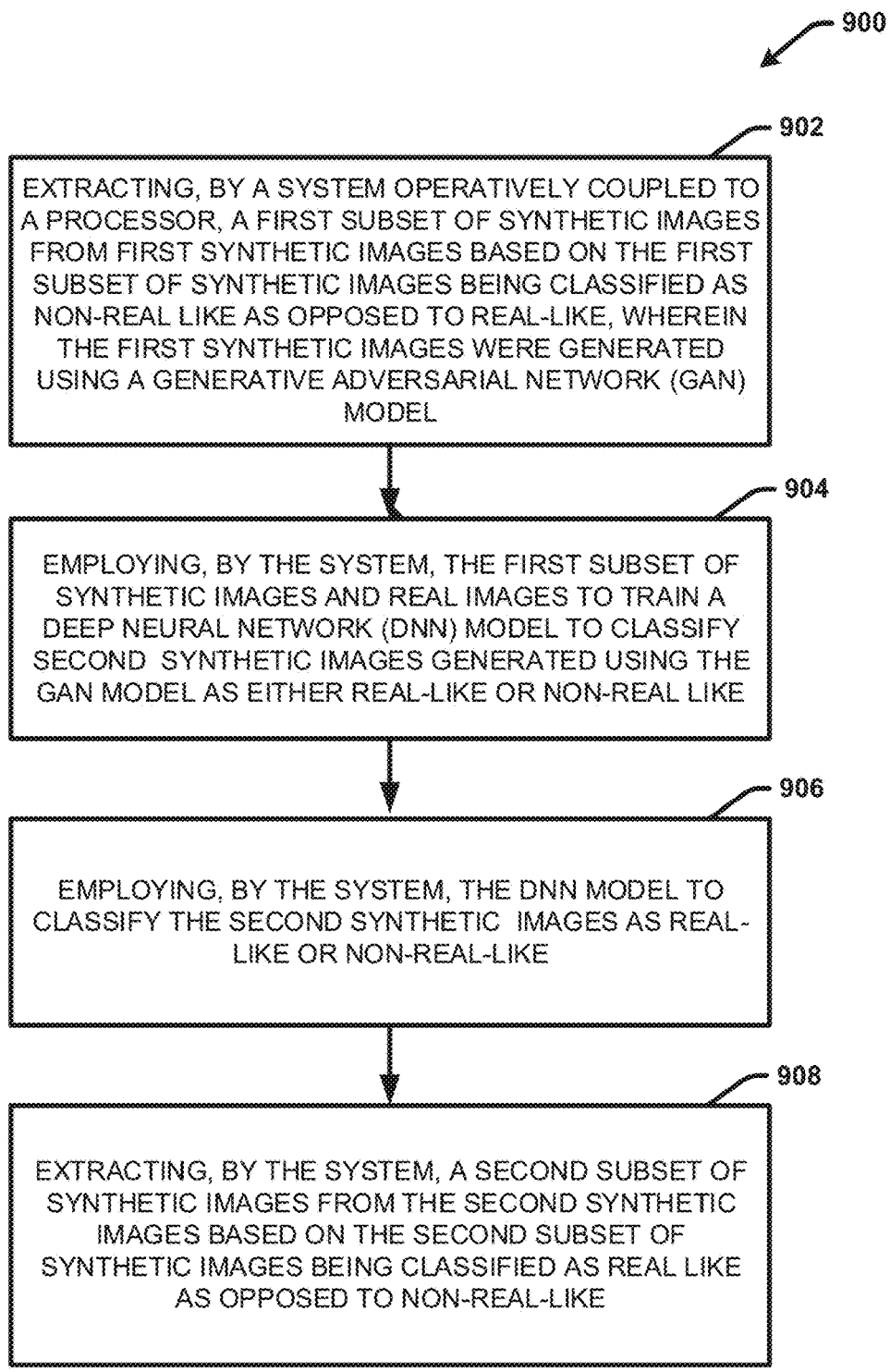
FIG. 9 provides a flow diagram of an example, non-limiting computer-implemented method for employing a DNN model to identify realistic synthetic images generated using a GAN model in accordance with one or more embodiments of the disclosed subject matter.

FIG. 9 provides a flow diagram of another example, non-limiting computer-implemented method 900 that facilitates DNN identification of realistic synthetic images generated using a GAN in accordance with one or more embodiments of the disclosed subject matter. Repetitive description of like elements employed in respective embodiments is omitted for sake of brevity.

At 902, a system operatively coupled to a processor (e.g., system 100 and/or system 400), can extract (e.g., using first extraction component 116) a first subset of synthetic images (e.g., non-real-like synthetic images 120) from first synthetic images (e.g., first synthetic images 110) based on the first subset of synthetic images being classified as non-real-like as opposed to real-like, wherein the first synthetic images were generated using a GAN model (e.g., GAN model 108). At 904, the system can employ the first subset of synthetic images and real images (e.g., real images 124) to train (e.g., using training component 122) a DNN model (e.g., DNN model 126) to classify second synthetic images generated using the GAN model as either real-like or non-real like. At 906, the system can employ the DNN model to classify the second synthetic images as real-like or non-real-like (e.g., using the inference component 406). At 908, the system can extract (e.g., using second extraction component 408), a second subset of synthetic images (e.g., real-like synthetic images 410) from the second synthetic based on the second subset of synthetic images being classified as real-like as opposed to non-real-like.

Figure 10:
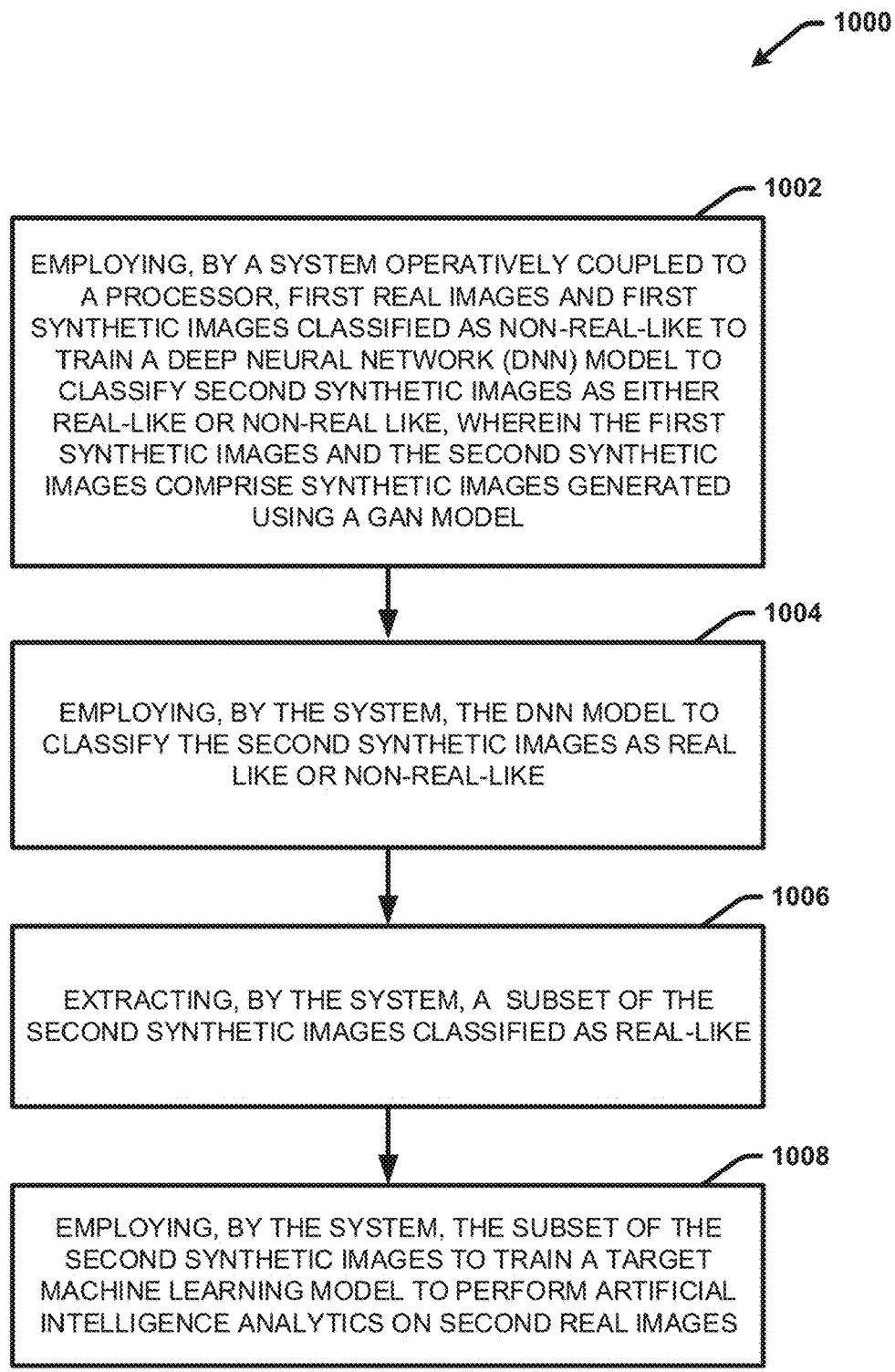
FIG. 10 provides a flow diagram of an example, non-limiting computer-implemented method for training a machine learning model using realistic synthetic images to make inferences on real images in accordance with one or more embodiments of the disclosed subject matter.

FIG. 10 provides a flow diagram of another example, non-limiting computer-implemented method 1000 that facilitates DNN identification of realistic synthetic images generated using a GAN in accordance with one or more embodiments of the disclosed subject matter. Repetitive description of like elements employed in respective embodiments is omitted for sake of brevity.

At 1002, a system operatively coupled to a processor (e.g., system 100, system 400 and/or system 600), can employ first real images (e.g., real images 124) and the first synthetic images classified as non-real-like (e.g., non-real-like synthetic images 120) to train (e.g., using training component 122) a DNN model (e.g., DNN model 126) to classify second synthetic images as either real-like or non-real like, wherein the first synthetic images and the second synthetic images comprise synthetic images generated using a GAN model (e.g., GAN model 108). At 1004, the system can employ the DNN model to classify the second synthetic images as real-like or non-real-like (e.g., using the inference component 406). At 1006, the system can extract (e.g., using second extraction component 408), a subset of the second synthetic images classified as real-like (e.g., real-like synthetic images 410). At 1008, the system can employ the subset of the second synthetic images to train (e.g., using target model training component 604) a target machine learning model (e.g., target model 606) to perform AI analytics on second real images.

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 11, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 11:
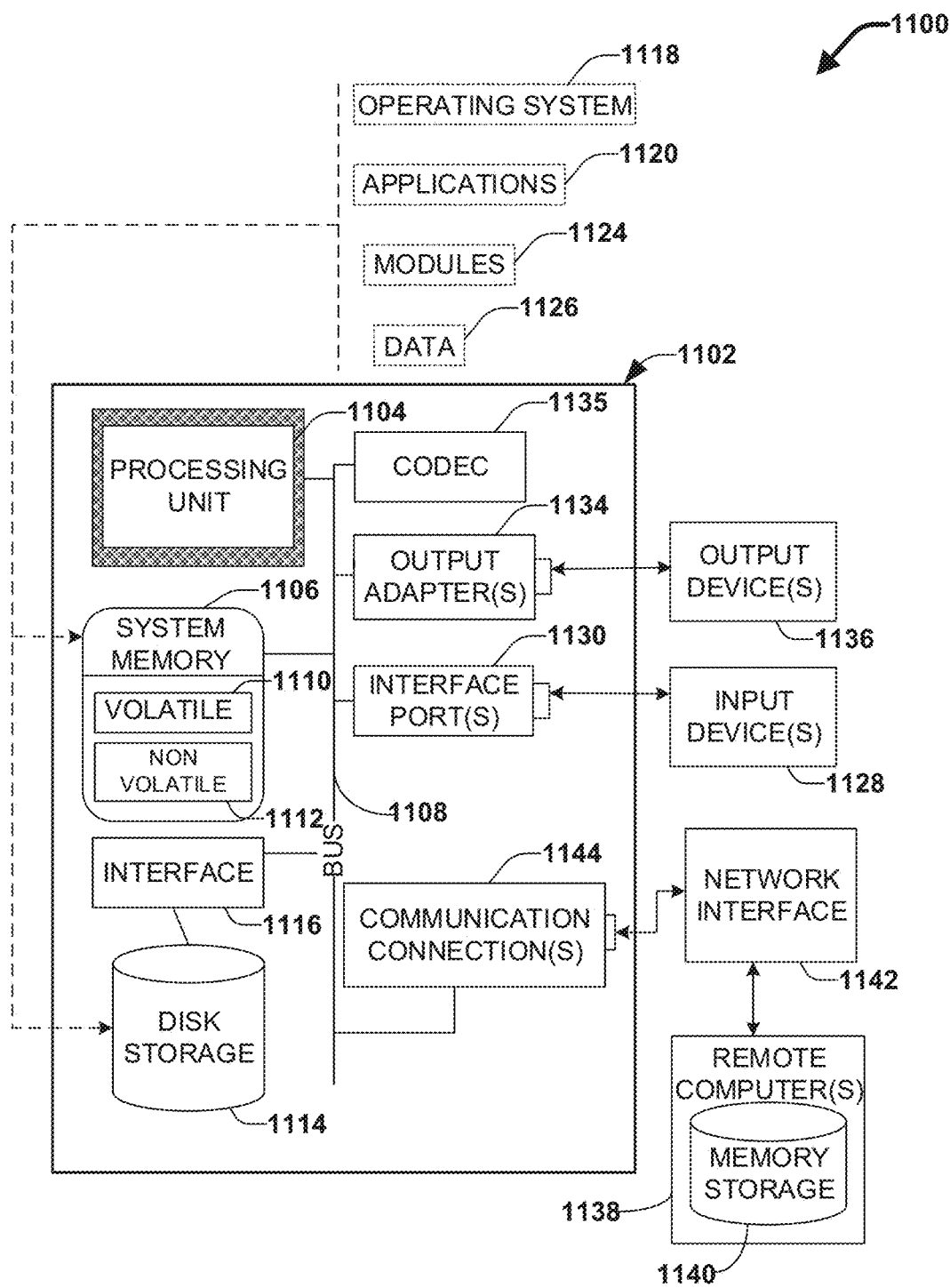
FIG. 11 illustrates a block diagram of an example, non-limiting operating environment in which one or more embodiments described herein can be facilitated.

With reference to FIG. 11, an example environment 1100 for implementing various aspects of the claimed subject matter includes a computer 1102. The computer 1102 includes a processing unit 1104, a system memory 1106, a codec 1135, and a system bus 1108. The system bus 1108 couples system components including, but not limited to, the system memory 1106 to the processing unit 1104. The processing unit 1104 can be any of various available processors. Dual microprocessors and other multiprocessor architectures also can be employed as the processing unit 1104.

The system bus 1108 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1106 includes volatile memory 1110 and non-volatile memory 1112, which can employ one or more of the disclosed memory architectures, in various embodiments. The basic input/output system (BIOS), containing the basic routines to transfer information between elements within the computer 1102, such as during start-up, is stored in non-volatile memory 1112. In addition, according to present innovations, codec 1135 can include at least one of an encoder or decoder, wherein the at least one of an encoder or decoder can consist of hardware, software, or a combination of hardware and software. Although, codec 1135 is depicted as a separate component, codec 1135 can be contained within non-volatile memory 1112. By way of illustration, and not limitation, non-volatile memory 1112 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1112 can employ one or more of the disclosed memory devices, in at least some embodiments. Moreover, non-volatile memory 1112 can be computer memory (e.g., physically integrated with computer 1102 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1110 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1102 can also include removable/non-removable, volatile/non-volatile computer storage medium. FIG. 11 illustrates, for example, disk storage 1114. Disk storage 1114 includes, but is not limited to, devices like a magnetic disk drive, solid state disk (SSD), flash memory card, or memory stick. In addition, disk storage 1114 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1114 to the system bus 1108, a removable or non-removable interface is typically used, such as interface 1116. It is appreciated that disk storage 1114 can store information related to a user. Such information might be stored at or provided to a server or to an application running on a user device. In one embodiment, the user can be notified (e.g., by way of output device(s) 1136) of the types of information that are stored to disk storage 1114 or transmitted to the server or application. The user can be provided the opportunity to opt-in or opt-out of having such information collected or shared with the server or application (e.g., by way of input from input device(s) 1128).

It is to be appreciated that FIG. 11 describes software that acts as an intermediary between users and the basic computer resources described in the suitable operating environment 1100. Such software includes an operating system 1118. Operating system 1118, which can be stored on disk storage 1114, acts to control and allocate resources of the computer 1102. Applications 1120 take advantage of the management of resources by operating system 1118 through program modules 1124, and program data 1126, such as the boot/shutdown transaction table and the like, stored either in system memory 1106 or on disk storage 1114. It is to be appreciated that the claimed subject matter can be implemented with various operating systems or combinations of operating systems.

A user enters commands or information into the computer 1102 through input device(s) 1128. Input devices 1128 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1104 through the system bus 1108 via interface port(s) 1130. Interface port(s) 1130 include, for example, a serial port, a parallel port, a game port, and a universal serial bus (USB). Output device(s) 1136 use some of the same type of ports as input device(s) 1128. Thus, for example, a USB port can be used to provide input to computer 1102, and to output information from computer 1102 to an output device 1136. Output adapter 1134 is provided to illustrate that there are some output devices 1136 like monitors, speakers, and printers, among other output devices 1136, which require special adapters. The output adapters 1134 include, by way of illustration and not limitation, video and sound cards that provide a means of connection between the output device 1136 and the system bus 1108. It should be noted that other devices or systems of devices provide both input and output capabilities such as remote computer(s) 1138.

Computer 1102 can operate in a networked environment using logical connections to one or more remote computers, such as remote computer(s) 1138. The remote computer(s) 1138 can be a personal computer, a server, a router, a network PC, a workstation, a microprocessor based appliance, a peer device, a smart phone, a tablet, or other network node, and typically includes many of the elements described relative to computer 1102. For purposes of brevity, only a memory storage device 1140 is illustrated with remote computer(s) 1138. Remote computer(s) 1138 is logically connected to computer 1102 through a network interface 1142 and then connected via communication connection(s) 1144. Network interface 1142 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1144 refers to the hardware/software employed to connect the network interface 1142 to the bus 1108. While communication connection 1144 is shown for illustrative clarity inside computer 1102, it can also be external to computer 1102. The hardware/software necessary for connection to the network interface 1142 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components; and
   a processor that executes the computer executable components stored in the memory, wherein the computer executable components comprise:
     a first extraction component that extracts, from first synthetic images, a subset of synthetic images classified as non-real like as opposed to real-like, wherein the first subset of synthetic images were generated using a generative adversarial network model; and
     a training component that employs the subset of synthetic images and real images to train a deep neural network model to classify second synthetic images generated using the generative adversarial network model as either real-like or non-real like:
     a synthetic image generator that generates third synthetic images using the generative adversarial network model; and
     an inference component that employs the deep neural network model to classify the third synthetic images as either real-like or non-real-like.

2. The system of claim 1, wherein the computer executable components further comprise:
   an annotation component that labels the first synthetic images as either real-like or non- real like, wherein the first extraction component extracts the subset of synthetic images from the first synthetic images in response to labeling of respective synthetic images included in the subset set as non-real like.

3. The system of claim 2, wherein the annotation component labels the first synthetic images based on reception of manual input that classifies the first synthetic images as either real-like or non-real-like.

4. The system of claim 1, wherein the subset of synthetic images comprises a first subset of synthetic images, and wherein the computer executable components further comprise:
   a second extraction component that extracts, from the third synthetic images, a second subset of synthetic images classified as real-like as opposed to non-real-like by the inference component.

5. The system of claim 4, wherein the real images comprise first real images and wherein the computer executable components further comprise:
   a target model training component that employs the third subset of synthetic images to train a machine learning model to perform artificial intelligence analytics on second real images.

6. The system of claim 5, wherein the first synthetic images, the second synthetic images, the third synthetic images, the first real images and the second real images comprise medical images, and wherein the target model training component employs the second subset of synthetic images to train the machine learning model to diagnose medical conditions reflected in the second real images.

7. The system of claim 4, wherein the real images comprise first real images and wherein the second extraction component combines the second subset of synthetic images with second real images to form a target model training dataset, and wherein the computer executable components further comprise:
   a target model training component that employs the target model training dataset to train a machine learning model to perform artificial intelligence analytics on third real images.

8. The system of claim 7, wherein the second subset of synthetic images the second real images, and the third real images comprise medical images, and wherein the target model training component employs the target model training dataset to train the machine learning model to diagnose medical conditions reflected in the third real images.

9. The system of claim 1, wherein the first synthetic images and the real images comprise medical images.

10. A method, comprising:
    extracting, from first synthetic images by a system operatively coupled to a processor, a subset of synthetic images classified as non-real like as opposed to real-like, wherein the first synthetic images were generated using a generative adversarial network model;
    employing, by the system, the subset of synthetic images and real images to train a deep neural network model to classify second synthetic images generated using the generative adversarial network model as either real-like or non-real like.
    generating, by the system, third synthetic images using the generative adversarial network model; and
    employing, by the system, the deep neural network model to classify the third synthetic images as either real-like or non-real-like.

11. The method of claim 10, wherein the deep neural network model comprises a very deep convolutional neural network.

12. The method of claim 10, further comprising:
    generating, by the system, the first synthetic images using the generative adversarial network model; and
    labeling, by the system, the first synthetic images as either real-like or non-real like, wherein the extracting comprises extracting the subset of synthetic images from the first synthetic images in response to labeling of respective synthetic images included in the subset set as non-real like.

13. The method of claim 12, wherein the labeling is based on reception of manual input that classifies the first synthetic images as either real-like or non-real-like.

14. The method of claim 12, further comprising:
classifying, by the system, the first synthetic images as either real-like or non-real-like using artificial intelligence, wherein the labeling is based on the classifying.

15. The method of claim 10, wherein the subset of synthetic images comprises a first subset, wherein the real images comprise first real images, and wherein the method further comprises:
extracting, by the system from the third synthetic images, a second subset of synthetic images classified as real-like as opposed to non-real-like by the deep neural network model; and
employing, by the system, the second subset of synthetic images to train a machine learning model to perform artificial intelligence analytics on second real images.

16. A machine-readable storage medium, comprising executable instructions that, when executed by a processor, facilitate performance of operations, comprising:
extracting, from first synthetic images, a subset of synthetic images classified as non-real like as opposed to real-like, wherein the first synthetic images were generated using a generative adversarial network model;
training a deep neural network model using the subset of synthetic images and real images to classify second synthetic images generated using the generative adversarial network model as either real-like or non-real like.
generating third synthetic images using the generative adversarial network model; and
employing the deep neural network model to classify the third synthetic images as either real-like or non-real-like.

17. The machine-readable storage medium of claim 16, wherein the subset of synthetic images comprises a first subset, wherein the real images comprise first real images, and wherein the operations further comprise:
extracting, from the third synthetic images, a second subset of synthetic images classified as real-like as opposed to non-real-like by the deep neural network model.

18. The machine-readable storage medium of claim 17, wherein the operations further comprise:
employing the second subset of synthetic images to train a machine learning model to perform artificial intelligence analytics on second real images.

19. The machine-readable storage medium of claim 16, wherein the operations further comprise:
generating the first synthetic images using the generative adversarial network model; and
labeling the first synthetic images as either real-like or non-real like, wherein the extracting comprises extracting the subset of synthetic images from the first synthetic images in response to labeling of respective synthetic images included in the subset set as non-real like.

20. The machine-readable storage medium of claim 16, wherein the first synthetic images, the second synthetic images, the third synthetic images and the real images comprise medical images.

\* \* \* \* \*